US00PP15930P3

(12) United States Plant Patent
Saunders

(10) Patent No.: US PP15,930 P3
(45) Date of Patent: Aug. 30, 2005

(54) ***SCAEVOLA* PLANT NAMED 'ZIG ZAG'**

(50) Latin Name: *Scaevola aemula*
Varietal Denomination: Zig zag

(76) Inventor: Rachel Saunders, Box 53108, Kenilworth, Cape Town (ZA)

( * ) Notice: Subject to any disclaimer, the term of this patent is extended or adjusted under 35 U.S.C. 154(b) by 619 days.

(21) Appl. No.: 10/112,971

(22) Filed: Mar. 27, 2002

(65) Prior Publication Data

US 2002/0157162 P1 Oct. 24, 2002

(51) Int. Cl.[7] ..... A01H 5/00

(52) U.S. Cl. ..... Plt./363

(58) Field of Search ..... Plt./263

*Primary Examiner*—Bruce R. Campell
*Assistant Examiner*—Michelle Kizilkaya

(57) ABSTRACT

A new cultivar of *Scaevola* named 'Zig Zag' that is characterized by a compact, creeping habit, and unique white lilac and purple flowers. In combination these traits set 'Zig Zag' apart from all other existing varieties of *Scaevola* known to the inventor.

2 Drawing Sheets

Latin name of the genus and species of the plant claimed: *Scaevola aemula.*

BACKGROUND OF THE INVENTION

The present invention relates to a new and distinct cultivar grown as an ornamental shrub for its compact cascading habit and unique bi-colored flowers. The new cultivar is known botanically as *Scaevola aemula* and will be referred to hereinafter by the cultivar name 'Zig Zag'.

'Zig Zag' is a sport and was discovered in the inventor's tissue lab, in the Republic of South Africa on October 1998. During production of a common blue-violet *Scaevola* (unpatented) several soma clonal variegations were planted in containers and kept in the laboratory to be observed. In 2000 the inventors selected one, for ornamental purposes, to plant in their trial garden. The selection was made based on its compact habit, unique flower color and bi-colored flower. In October of 2000 'Zig Zag' generated commercial interest. This has resulted in the establishment of a new breeding program to create new flower colors with the bi-color benefits and habit benefits.

The closest comparison plants are the common varieties of *Scaevola* including 'New Dawn', 'Blue Wonder' and 'Blue Shamrock' (all unpatented). 'Zig Zag' is distinguishable from the comparison plants by its compact habit, unique bi-colored flower and flower color of white lilac and purple.

The first asexual reproduction of 'Zig Zag' was conducted in a tissue lab by the inventor in November 2000 in Congleton, United Kingdom. The method used for asexual propagation was stem cuttings. The characteristics of the new cultivar have been determined stable and are reproduced true to type in successive generations.

SUMMARY OF THE INVENTION

The following traits have been repeatedly observed and represent the characteristics of the new *Scaevola* cultivar 'Zig Zag'. These traits in combination distinguish 'Zig Zag' from all other commercial varieties known to the inventor. 'Zig Zag' has not been tested under all possible conditions and phenotypic differences may be observed with variations in environmental, climatic and cultural conditions.

1. *Scaevola* 'Zig Zag' exhibits a compact habit with creeping and cascading branches.
2. *Scaevola* 'Zig Zag' exhibits unique bi-colored flowers that are white-lilac and purple in color.
3. *Scaevola* 'Zig Zag' is 92 cm. in width and 41 cm. in height at maturity.
4. *Scaevola* 'Zig Zag' is propagated by stem cuttings.
5. *Scaevola* 'Zig Zag' is an ornamental used in the landscape and in hanging baskets.
6. *Scaevola* 'Zig Zag' blooms spring, summer and autumn.

BRIEF DESCRIPTION OF THE DRAWINGS

The accompanying drawings illustrate the distinguishing traits of the new cultivar 'Zig Zag'.

Sheet 1 illustrates the entire plant in bloom from a side perspective.

Sheet 2 shows a close-up view of the flowers and leaves. The drawings were made in July of plants grown in Arroyo Grande, Calif. in seven-gallon containers out-of-doors. The drawings were made using conventional techniques and although colors may appear different from actual colors due to light reflectance they are as accurate as possible by conventional photography.

BOTANICAL DESCRIPTION OF THE PLANT

The following is a detailed description of 'Zig Zag' as grown in seven-gallon containers out-of-doors in Arroyo Grande, Calif. The color determinations are in accordance with The R.H.S. Colour Chart of The Royal Horticultural Society, London, England, except where general color terms of ordinary dictionary significance are used. Growing conditions, diseases and pests are similar to that of other *Scaevola*. There are no growing problems known to the inventor.

Botanical classification: *Scaevola aemula* 'Zig Zag'.
Species: Aemula.

Commercial classification: Perennial.
Use: Ornamental for hanging basket, container or landscape.
Cultural requirements: Plant in full sun with moderate to regular water and any free-draining soil.
Parentage: *Scaevola* 'Zig Zag' is a sport of the parent plant *Scaevola aemula*.
Plant description:
*Bloom period.*—Spring, summer and autumn.
*Plant habit.*—Compact shrub.
*Vigor.*—Vigorous.
*Sexuality.*—Perfect.
*Height.*—92 cm. in width and 41 cm. in height at maturity.
*Hardiness.*—USDA Zone 10.
*Root system.*—Fine.
*Propagation.*—Propagation is accomplished using soft cuttings.
*Time to develop roots.*—3 weeks is needed to produce roots on an initial cutting.
*Crop time.*—Ten weeks are needed to produce a finished four-inch container from a rooted cutting.
Stem:
*Shape.*—Cylindrical and columnar.
*Stem color.*—146D suffused with 59A.
*Stem dimensions.*—92 cm. in width and 41 cm. in height.
*Basal stem diameter.*—0.75 cm. in diameter.
*Stem surface.*—Glabrous and shiny.
*Branching.*—Basal branching, cascading and procumbent.
*Internode length.*—4 cm. between nodes.
Foliage:
*Type.*—Evergreen.
*Arrangement.*—Alternate.
*Shape.*—Oblanceolate.
*Division.*—Simple.
*Apex.*—Apiculate.
*Base.*—Truncate.
*Venation.*—Mid vein prominent, depressed on adaxial surface and protruding on abaxial surface.
*Vein color* (*abaxial surface*).—138B.
*Vein color* (*adaxial surface*).—138A.
*Young leaf margins.*—Entire with sparse minute hairs and 2 or three minute teeth.
*Mature leaf margins.*—Erose.
*Texture.*—Flexible.
*Attachment.*—Sheathing.
*Leaf surfaces* (*adaxial and abaxial*).—Slightly pubescent.
*Mature leaf dimensions.*—10 cm. in length and 3 cm. in width and cupped.
*Young leaf dimensions.*—1.75 cm. in length and 0.75 cm. in width and flat.
*Mature leaf color* (*adaxial surface*).—137A.
*Mature leaf color* (*abaxial surface*).—146B.
*Young leaf color* (*adaxial surface*).—137A with tips of 59A.
*Young leaf color* (*abaxial surface*).—146B with tips of 59A.
*Fragrance.*—Absent.
Flowers:
*Type.*—Inflorescence.
*Shape.*—A combination of cruciform and explanate.
*Flower dimensions.*—20–27 mm. in width and 10–12 mm. in height.
*Inflorescence type.*—Raceme.
*Persistent or self-cleaning.*—Self-cleaning.
*Aspect.*—Facing upward and outward.
*Throat depth.*—15 mm. in depth.
*Fragrance.*—None.
*Sexuality.*—Bisexual.
*Petals.*—Five in number.
*Petal color.*—Dark centers ranging from 80A to 82B in the center of the petal and a white background of 155A.
*Throat color.*—2A with veins of 82A and hairs at opening of throat that are 2A.
*Fused or unfused.*—Unfused.
*Petal dimensions.*—1 cm. in length and 0.50 cm. in width.
*Petal shape.*—Oblanceolate.
*Petal margin.*—Entire.
*Petal apex.*—Apiculate.
*Petal surface* (*abaxial surface*).—Glabrous on edges and pubescent on center dark purple area.
*Petal surface* (*adaxial surface*).—Glabrous.
*Calyx.*—Minute and adnate to ovary.
Reproductive organs:
*Stamens.*—Five rudimentary stamens.
*Stamen color.*—165B.
*Stamen dimensions.*—6 mm. in length and 0.25 mm. in diameter.
*Anther color.*—165B.
*Anther dimensions.*—0.50 mm. in width and 3 mm. in length.
*Pistil.*—One.
*Pistil dimensions.*—12 mm. in length and 1 mm. in diameter.
*Pistil color.*—59A.
*Stigma shape.*—Brush with bifid lip.
*Stigma color.*—2B.
*Stigma dimensions.*—1–2 mm. in diameter and 1 mm. in length.
*Ovary position.*—Inferior.
*Ovary color.*—138B.
*Ovary shape.*—Oval.
*Ovary dimensions.*—1.25 mm. in height and 1 mm. in diameter.
Seed production: No seed production has been observed.

I claim:

1. A new and distinct cultivar of *Scaevola* plant named 'Zig Zag' as described and illustrated herein.

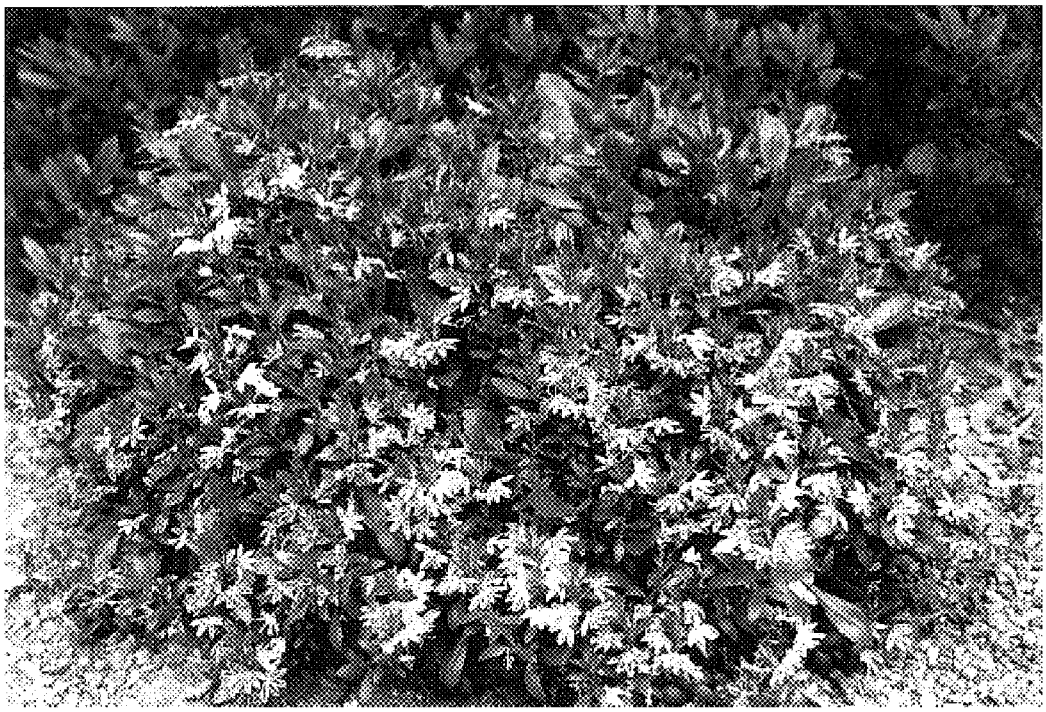

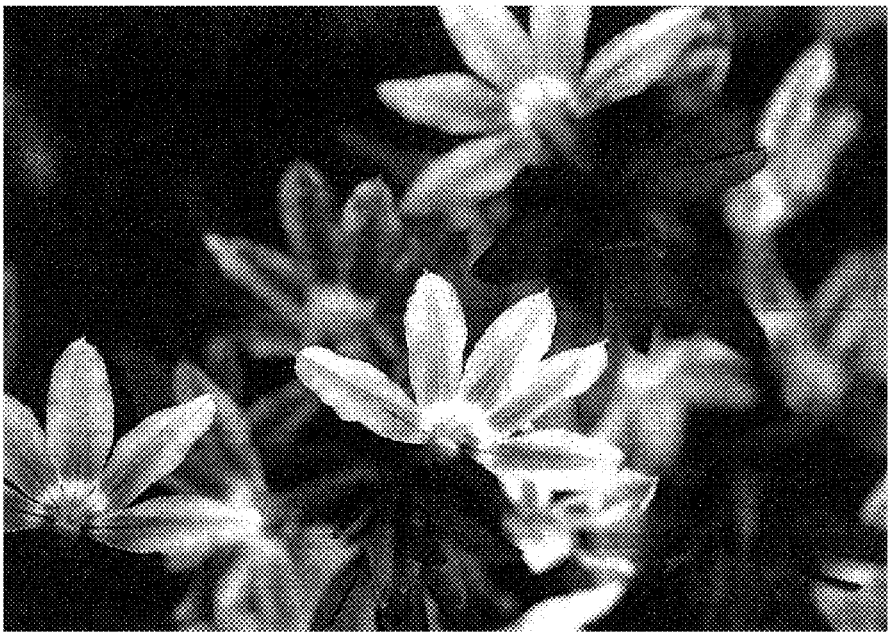

* * * * *